US006492492B1

(12) United States Patent
Stayton (10) Patent No.: US 6,492,492 B1
(45) Date of Patent: Dec. 10, 2002

(54) CIRCULARLY PERMUTED BIOTIN BINDING PROTEINS (75) Inventor: Patrick S. Stayton, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/285,867

(22) Filed: Apr. 2, 1999

Related U.S. Application Data (60) Provisional application No. 60/080,560, filed on Apr. 3, 1998.

(51) Int. Cl.$^7$ .............................................. C07K 14/00

(52) U.S. Cl. ..................... 530/350; 536/23.1; 536/23.4; 536/23.7; 435/69.1; 530/825

(58) Field of Search ................................ 530/350, 825; 536/23.1, 23.4, 23.7; 435/69.1

(56) References Cited

U.S. PATENT DOCUMENTS

| 4,458,066 A | 7/1984 | Caruthers et al. |
| 4,839,293 A | 6/1989 | Cantor et al. |
| 5,135,876 A | 8/1992 | Andrade et al. |
| 5,168,049 A | 12/1992 | Meade et al. |
| 5,215,927 A | 6/1993 | Berenson et al. |
| 5,252,466 A | 10/1993 | Cronan, Jr. |
| 5,272,254 A | 12/1993 | Meade et al. |
| 5,328,985 A | 7/1994 | Sano et al. |
| 5,449,759 A | 9/1995 | Hoffman et al. |
| 5,489,528 A | 2/1996 | Kopetzki et al. |
| 5,624,896 A | 4/1997 | Axworthy et al. |
| 5,635,599 A | 6/1997 | Pastan et al. |
| 5,672,691 A | 9/1997 | Kopetzki et al. |
| 5,681,745 A | 10/1997 | Szfranski et al. |

FOREIGN PATENT DOCUMENTS

| DE | 196 37 718 A1 | 10/1997 |
| EP | 198015 B2 | 7/1995 |
| WO | WO87/05026 A1 | 8/1987 |
| WO | WO89/03422 | 4/1989 |
| WO | WO93/09144 | 10/1992 |
| WO | WO95/27732 A2 | 10/1995 |

OTHER PUBLICATIONS

Argarana et al., "Molecule Cloning and Nucleotide Sequence of the Streptavidin Gene," Nucl. Acids Res. 14:1871–1882 (1986).
Asai, Methods in Cell Biology vol. 37: Antibodies in Cell Biology, Academic Press, Inc.:New York, 1993.
Ay, et al., "Crystal structures and properties of de novo circularly permuted 1,3–4,4–beta–glucanses," Proteins 30(2):155–167 (1998).
Barany & Merrifield, "Solid–Phase Peptide Synthesis" in The Peptides: Analysis, Synthesis, Biology vol. 2. Special Methods in Peptide Synthesis, Part A, pp. 3–284.
Batra, et al., "Single–chain immunotoxins directed at the human transferrin receptor containing Pseudomonas exotoxin A or diphtheria toxin: anti–TFR(Fv)–PE40 and DT388–anti–TFR(Fv)," Mol. Cell Biol. 11(4):2200–5 (1991).
Bayer, et al., "A sensitive assay for biotin, avidin and streptavidin," Analytical Biochemistry 154:367–370 (1986).
Beaucage, et al., "Deoxynucleoside phosphoramidites–a new class of key intermediates for deoxypolynucleotide synthesis," Tetra. Lett. 22:1859–1862 (1981).
Brinkmann, et al., "B3(Fv)–PE38KDEL, a single–chain immunotoxin that causes complete regression of a human carcinoma in mice," Proc. Natl. Acad. Sci. USA 88:8616–8620 (1991).
Brown, et al., "Chemical synthesis and cloning of a tyrosine tRNA gene," Meth. Enzymol. 68:109–151 (1979).
Brunger, "Free R value: a novel statistical quantity for assessing the accuracy of crystal structures," Nature 355:472–475 (1992).
Chaudhary, et al., "A rapid method of cloning functional variable–region antibody genes in Escherichia coli as single–chain immunotoxins," Proc. Natl. Acad. Sci. USA 87:1066–1070 (1990).
Chaudhary, et al., "A recombinant immunotoxin consisting of two antibody variable domains fused to Pseudomonas exotoxin," Nature 339:394–397 (1989).
Chilkoti, et al., "Site–specific Conjugation of a Smart Polymer to a Genetically Engineered Protein," Bioconjugate Chem. (1993).
Chilkoti, et al., "Molecular origins of the slow streptavidin–biotin dissociation kinetics," Am Chem Soc 117:10622–10628 (1995).

(List continued on next page.)

Primary Examiner—Donna C. Wortman
Assistant Examiner—Robert A. Zeman
(74) Attorney, Agent, or Firm—Holland & Knight LLP (57) ABSTRACT Circularly permuted proteins are described wherein the natural termini of the polypeptide are joined and the resulting circular protein is opened at another point to create new C- and N- termini. The resulting protein exhibits some altered characteristic such as reduced substrate binding, for example. Fusion proteins can be made from the circularly permuted protein by attaching the second polypeptide to these newly created termini. These fusion proteins will have altered properties from a fusion protein made by attaching the second polypeptide to the natural termini. For example, the second peptide or protein can be attached at a position where it is more accessible to its substrate or intended target. In the preferred embodiment, the base circularly permuted biotin binding protein. In one embodiment, a flexible polypeptide loop important for the binding of biotin was opened by creation of the circularly permuted protein. The original termini (residues 13 and 139 of SEQ ID NO:1) were joined by a linker. The biotin association constant was reduced approximately six orders of magnitude below that of wild type streptavidin to $10^7$ $M^{-1}$. Fusion proteins of the circularly permuted streptavidin can be made with secondary peptides/proteins such as IgG binding protein A or single-chain antibodies.

12 Claims, 6 Drawing Sheets

OTHER PUBLICATIONS

Chilkoti, et al., "Site–directed mutagenesis studies of the high–affinity streptavidin–biotin complex: contributions of tryptophan residues 79, 108, and 120," *Proc Natl Acad Sci USA* 92:1754–1758 (1995).

Chu, et al., "Thermodynamic and structural consequence of flexible loop deletion by circular permutation in the streptavidin–biotin system," *Protein Science* 7:848–859 (1998).

Dubel, et al., "Bifunctional and multimeric complexes of streptavidin fused to single chain antibodies (scFv)," *J. Immul. Methods*. 178:201–209 (1995).

Engh, et al., "Accurate bond and angle parameters for x–ray protein structure refinement," *Acta Crystallogr* A47:392–400 (1991).

Erijman & Weber, "Oligomeric Protein Associations: Transition from Stochastic to Deterministic Equilibrium," *Biochemistry* 30:1595–1599 (1991).

Erijman & Weber, "Use of Sensitized Fluorescence for the Study of the Exchange of Subunits in Protein Aggregates," *Photochem. Photobiol*. 57:411–415 (1993).

Falzone, et al., "Dynamics of a flexible loop in dihydrofolate reductase from *Escherichia coli* and it implication for catalysis," *Biochemistry* 33:439–442 (1994).

Freitag, et al., "Structural studies of the streptavidin binding loop," *Protein Sci* 6:1157–1166 (1997).

Gitlin, et al., "Studies on the biotin–binding site of streptavidin. Tryptophan residues involved in the active site," *Biochem J*. 256:279–282 (1988).

Goldenberg, et al., "Circular and circularly permuted forms of bovine pancreatic trypsin inhibitor," *J Mol Biol* 165:407–413 (1983).

Graf, et al., "Random circular permutation of genes and expressed polypeptide chains: application of the method to the catalytic chains of aspartate transcarbamoylase," *Proc. Natl Acad Sci USA* 93:11591–11596 (1996).

Heinemann, et al., "Circular permutation of polypeptide chains: implications for protein folding and stability," *Prog Biophys Molec Biol* 64:122–143 (1995).

Hendrickson, et al., "Crystal structure of core streptavidin determined from multiwavelength anomalous diffraction of synchrotron radiation," *Proc Natl Acad Sci USA* 86:2190–2194 (1989).

Horlick, et al., "Permuteins of interleukin 1 beta—a simplified approach for the construction of permutated proteins having new termini," *Protein Eng* 5:427–431 (1992).

Hutchinson, et al., "PROMOTIF—a program to identify and analyze structural motifs in proteins," *Protein Sci* 5:212–200 (1996).

Jia, et al., "Crystal structure of transaldolase B from *Escherichia coli* suggests a circular permutation of alpha/beta barrel within the class I aldolase family," *Structure* 4(6):715–724 (1996).

Jin, et al., "High Resolution Functional Analysis of Antibody–Antigen Interactions," *J. Mol. Biol*. 226:851–865 (1992).

Kurzban, et al., "The Quaternary Structure of Streptavidin in Urea," *J. Biol. Chem*. 266:14470–14477 (1991).

Laskowski, et al., "Procheck: a program to check the stereochemical quality of protein structures," *J Appl Crystallogr* 26:283–291 (1993).

Lindqvist, et al., "Circular permutations of natural protein sequences: structural evidence," *Curr Opinion Struc Biol* 7:422–427 (1997).

Luger, et al., "Correct folding of circularly permuted variants of a beta alpha barrel enzyme in vivo," *Science* 243:206–210 (1989).

Matthews & Van Holde, Biochemistry, Chap. 5, pp. 137–141, Benjamin/Cummings Publish. Co. California (1990).

McRee. "A visual protein crystallographic software system for X11/Xview," *J Mol Graph* 10:44–46 (1992).

Merrifield, et al., "Solid phase peptide synthesis. I. The synthesis of a tetrapeptide," *J. Am. Chem. Soc*. 85:2149–2156 (1963).

Meyer, et al., "Streptavidin–Biotin immunotoxins: A New Approach to Purging Bone Marrow," *Exp. Hematol*. 19:710–713 (1991).

Miyamoto & Kollman, "What Determines the Strength of Noncovalent Association of Ligands to Proteins in Aqueous Solution?" *Proc. Natl. Acad. Sci. USA* 90:8402–8406 (1993).

Miyamoto, et al., "Absolute and Relative Binding Free Energy Calculations of the Interaction of Biotin and Its Analogs with Streptavidin Using Molecular Dynamics/Free Energy Perturbation Approaches," *Proteins* 16:226–245 (1993).

Moews, et al., "Refinement of the structural of carp muscle calcium–binding parvalbumin by model building and difference Fourier analysis," *J Mol Biol* 91:201–225 (1975).

Morton, et al., "Specificity of ligand binding in a buried nonpolar cavity of T4 lysozyme: linkage of dynamics and structural plasticity," *Biochemistry* 34:8576–8588 (1995).

Murphy, et al., "Structural energetics of peptide recognition: angiotensin II/antibody binding," *Proteins* 15:113–120 (1993).

Narang, et al., "Improved phosphotriester method for the synthesis of gene fragments," *Meth. Enzymol*. 68:90–98 (1979).

Navaza, "AMoRe: an automated package for molecular replacement," *Acta Crystallogr* A50:157–163 (1994).

Noble, et al., "Structures of the "open" and "closed" state of trypanosomal triosephosphate isomerase, as observed in a new crystal form: implications for the reaction mechanism," *Proteins* 16:311–326 (1993).

Pan & Uhlenbeck, "Circularly permuted DNA, RNA, and proteins—a review," *Gene* 125 (2):111–14 (1993).

Parkin, et al., "XABS2: an empirical absorption correction program," *J Appl Crystallogr* 28:53–56 (1995).

Read, "Improved fourier coefficients for maps using phases for partial structures with errors," *Acta Crystallogr* A42:140–149 (1986).

Sano & Cantor, "A Streptavidin–Protein A Chimera That Allows One–Step Production of a Variety of Specific Antibody Conjugates," *Bio/Technology* 9:1378–1381 (1991).

Sano & Cantor, "Expression Vectors for Streptavidin–Containing Chimeric Proteins," *Biochem. Biophys. Res. Commun*. 176:571–577 (1991).

Sano, et al., "A streptavidin–metallothionein chimera that allows specific labeling of biological materials with many different heavy metal ions," *Proc Natl Acad Sci USA* 89:1534–1538 (1992).

Sano, et al., "Expression of a cloned streptavidin gene in *Escherichia coli*," *Proc Natl Acad Sci USA* 87:142–146 (1990).

Savage, et al., Avidin–Biotin Chemistry: A Handbook, Pierce Chemical Co. (1992).

Schwartz, et al., "Observation of Noncovalent Complexes to the AvidinTetramer by Electrospray Ionization Mass Spectrometry," *J. Amer. Soc. Mass Spectrom.* 5:201–204 (1994).

Sligar, et al., "Mutagenesis of Cytochromes P450cam and $b_5$," *Meth. Enzymol.*, 206:31–49 (1990).

Sowdhamini, et al., "Stereochemical Modeling of Disulfide Bridges. Criteria for Introduction into Proteins by Site–directed Mutagenesis," *Protein Eng.* 3:95–103 (1989).

Spolar, et al., "Coupling of local folding to site–specific binding of proteins to DNA" *Science* 263:777–784 (1994).

Takei, et al., "Temperature Responsive Bioconjugates. 1. Synthesis of Temperature–Responsive Oligomers with Reactive End Groups and Their Coupling to Biomolecules," *Bioconjugate Chem.* 4:42–46 (1993).

Tanaka, et al., "Mutational and proteolytic studies on a flexible loop in glutathione synthetase from *Escherichia coli* B: the loop and arginine 233 ar critical for the catalytic reaction," *Biochemistry* 31:2259–2265 (1992).

Uversky, et al., "Circularly permuted dihrdrofolate reductase possesses all the properties of the molten globule state, but can resume functional tertiary structure by interaction with its ligands," *Protein Sci.* 5:1844–51 (1996).

Vignais, et al., :"Circular permutation within the coenzyme binding domain of the tetrameric glyceraldehyde–3–phosphate dehydrogenase from *Bacillus stearothermophilus*," *Protein Sci.* 4:994–1000 (1995).

Voss & Skerra, "Mutagenesis of a flexible loop in streptavidin leads to higher affinity for the Strep–tag II peptide and improved performance in recombinant protein purification," *Protein Engineering* 10:975–982 (1993).

Weber, et al., "Structural origins of high–affinity biotin binding to streptavidin," *Science* 243:85–88 (1989).

Wierenga, et al., "The crystal structure of the "open" and the "closed" conformation of the flexible loop of trypanosomal triosephosphate isomerase," *Proteins* 10:33–49 (1991).

Wilchek & Bayer, "Introduction to Avidin–Biotin Technology," *Meths. Enzymol.* 184:5–45 (1990).

Willner, et al., "Photoswitchable Binding of Substrates to Proteins: Photoregulated Binding of a α–D–Mannopyranose to Concanavalin A Modified by a Thiophenefulgide Dye," *J. Am. Chem. Soc.* 114:3150–3151 (1992).

Yang, et al., "Aspartate transcarbamoylase containing circularly permuted catalytic polypeptide chains," *Proc Natl Acad Sci USA* 90:11980–11984 (1993).

Zhang, et al., "Circular permutation of T4 lysozyme," *Biochemistry* 32:12311–12318 (1993).

Zoller, et al., "Oligonucleotide–directed mutagenesis of DNA fragments cloned into M13 vectors," *Meth. Enzymol.* 100:468–500 (1983).-

CIRCULARLY PERMUTED BIOTIN BINDING PROTEINS

CROSS-REFERENCE TO RELATED APPLICATION

This application claims benefit of U.S. Provisional Application No. 60/080,560, filed Apr. 3, 1998.

STATEMENT REGARDING FEDERALLY FUNDED RESEARCH

The U.S. government has certain rights in this invention by virtue of National Institutes of Health grant DK49655 to Patrick Stayton.

FIELD OF THE INVENTION

The present invention is in the field of modified streptavidin, and more particularly in the area of streptavidin fusion proteins wherein the base polypeptide is streptavidin having a circularly permuted loop.

BACKGROUND OF THE INVENTION

Fusion proteins are polypeptide chains consisting of two or more polypeptides fused together into a single polypeptide chain. Streptavidin fusion proteins have been reported, for example, that combine the biotin binding capabilities of streptavidin with that of a second protein, such as IgG-binding protein A (Sano and Cantor, Bio/Technology 9:1377–1381 (1992), and U.S. Pat. No. 5,328,985 to Sano et al.), metallothionein (Sano, et al., P. N. A. S. USA 89:1534–1538 (1992)), single chain antibodies (Dubel et al., J. Immul. Methods. 178:201–209 (1995)) and the human low density lipoprotein (LDL) receptor (U.S. Pat. No. 4,839,293 to Cantor et al.). These proteins include wild-type streptavidin attached to the second protein. Tight binding of biotin to the streptavidin is substantially maintained.

The high affinity of streptavidin for biotin, with a $K_a$ of approximately $2.5 \times 10^{13}$ $M^{-1}$, has been advantageously utilized in many existing diagnostic and separation technologies, and in targeted drug/imaging agent delivery systems. However, the extremely high affinity of streptavidin for biotin can be detrimental in applications where reversible immobilization of streptavidin or biotinylated targets is ultimately desirable. An important example is affinity separations, where a biotinylated target molecule is captured with streptavidin and where subsequent release and recycling of the biotinylated target or capture agent (e.g. antibody) is desired. Similarly, in drug delivery applications where the streptavidin-biotin system forms the targeting and/or delivery component, the exceptionally slow biotin dissociation kinetics limits potential applications utilizing diffusion of the biotinylated imaging agent or drug to the therapeutic target, and may also result in slow in vivo clearance of biotinylated imaging agents.

In common with many other high-affinity protein-ligand systems, streptavidin utilizes three key molecular recognition mechanisms in its interaction with biotin: an extensive hydrogen bonding network, several direct aromatic side-chain contacts, and a flexible loop near the biotin binding site. Flexible loops are protein structural elements often found near the binding sites or active sites of receptors and enzymes. With many flexible loops, ligand binding is accompanied by a open-to-closed (or disorder-to-order) conformation change in going from the unbound to the ligand-bound state (Noble M E M et al. (1993) Proteins 16:311–326; Wierenga R K, et al. (1991) Proteins 10:33–49; Morton A, et al. (1995) Biochemistry 34:8576–8588; Tanaka T, et al. (1992) Biochemistry 31:2259–2265; and Falzone C J, et al. (1994) Biochemistry 33:439–442). The loops presumably play an important role in gating ligand association and dissociation, but their energetic contributions to molecular recognition remain unclear. The free energy of binding is the result of balancing the entropic costs/benefits of ordering of loops and release of bound water with the enthalpic benefits of burying non-polar surface area and establishing bonding contacts. It is expected that protein-ligand interactions will lead to energetic signatures similar to those associated with protein folding. Murphy K P, et al. (1993) Proteins 15:113–120; Spolar R S, et al. (1994) Science 263:777–784.

A prominent feature accompanying biotin association is the conformational change of a flexible binding loop (Hendrickson W A, et al. (1989) Proc Natl Acad Sci USA 86:2190–2194; Weber P C, et al. (1989) Science 243:85–88). A crystallographic study of the flexible loop in core streptavidin has been reported (Freitag S, et al. (1997) Protein Sci 6:1157–1166). The loop (residues 45–52 of SEQ ID NO:1) is in a closed conformation in the presence of biotin and in an open conformation in apo-streptavidin. Residues 49 through 52 (SEQ ID NO:1) are found in a $3_{10}$ helix and the open conformation is stabilized by a hydrogen bonding interaction between residues 45 and 52 (SEQ ID NO:1). In a tetragonal crystal form, these residues are disordered in the open conformation (Weber P C, et al. (1989) Science 243:85–88). Ser45 (SEQ ID NO:1) terminates the β-strain leading into the loop and the side-chain oxygen of this residue is hydrogen-bonded to one of the ureido-oxygen of biotin, and the backbone amide nitrogen of Asn49 (SEQ ID NO:1) is hydrogen-bonded to the biotin carboxylate. The rearrangement and/or deletion of this loop can lead to many changes, particularly changes in binding of substrate. For many enzymes, it may be useful to alter binding characteristics, such as, for example, increasing or decreasing binding affinity.

Circular permutation is a technique wherein the normal termini of a polypeptide are linked and new termini are created by breaking the backbone elsewhere. In many polypeptides, the normal termini are in close proximity and can be joined by a short amino acid sequence. The break in the polypeptide backbone can be at any point, preferably at a point where the natural function and folding of the polypeptide are not destroyed. Circular permutation creates new C- and N-termini, allowing creation of fusion proteins wherein the fused peptide or protein is attached at a different place on the host protein. For example, if the natural termini are at the interior of the base protein, it may be disruptive to attach a peptide or protein at the natural termini, By changing the attachment location to a place near the exterior of the host protein, stability of the host protein may be maintained. In some situations, disruption of a loop near the binding site may advantageously disrupt substrate binding.

It would be advantageous to provide streptavidin mutants having a lower binding affinity for biotin than wild type streptavidin. It would be advantageous to provide streptavidin fusion proteins having a lower binding affinity for biotin than fusion proteins including wild type streptavidin.

It would be advantageous to provide streptavidin fusion proteins wherein the second peptide or protein is attached at a more useful position.

BRIEF SUMMARY OF THE INVENTION

Circularly permuted proteins are described wherein the natural termini of the polypeptide are joined and the resulting circular protein is opened at another point to create new C- and N- termini. The resulting protein exhibits some altered characteristic such as reduced substrate binding, for example. Fusion proteins can be made from the circularly permuted protein by attaching the second polypeptide to these newly created termini. These fusion proteins will have altered properties from a fusion protein made by attaching the second polypeptide to the natural termini. For example, the second peptide or protein can be attached at a position where it is more accessible to its substrate or intended target. In the preferred embodiment, the base polypeptide is streptavidin. Circular permutation of streptavidin results in a circularly permuted biotin binding protein. In one embodiment, a flexible polypeptide loop important for the binding of biotin was opened by creation of the circularly permuted protein. The original termini (residues 13 and 139 of SEQ ID NO:1) were joined by a linker. The biotin association constant was reduced approximately six orders of magnitude below that of wild type streptavidin to $10^7$ $M^{-1}$. Fusion proteins of the circularly permuted streptavidin can be made with secondary peptides/proteins such as IgG binding protein A or single-chain antibodies.

DETAILED DESCRIPTION OF THE INVENTION

1. Design of the Circularly Permuted Protein

Circularly permuted proteins have provided an experimental means of investigating the biophysical consequences of loop rearrangement or removal on ligand binding in ways not available using traditional deletion mutants. Circularly permuted proteins have been used previously to investigate the protein folding problem (Yang Y, et al. (1993) Proc Natl Acad Sci US. 90:11980–1984; Graf R, et al. (1996) Proc Natl Acad Sci USA 93:11591–11596), and naturally occurring and synthetic circularly permuted proteins have been identified (Heinemann U, et al. (1995) Prog Biophys Molec Biol 64:122–143; Lindqvist Y, et al. (1997) Curr Opinion Struc Biol 7:422–427; Goldenberg D P, et al. (1983) J Mol Biol 164:407–413; Luger K, et al. (1989) Science 243–206–209). U.S. Pat. No. 5,635,599 to Pastan et al. discloses fusion proteins created from circularly permuted interleukin 4 (IL4).

Circular permutants generally are created by disrupting the polypeptide chain at a selected point to create new termini and bridging the two natural termini either directly or through a linker such as an amino acid linker. Circular permutation thus has the effect of essentially preserving the sequence and identity of the amino acids of a protein while generating new termini at different locations. Moreover, the tertiary structure of the protein is generally conserved. Although a circularly permuted protein can be made chemically, it is preferably created by recombinant techniques.

There are two general requirements for the creation of a circularly permuted protein that retains its native biological activity: 1) the termini in the native protein must be favorably located so that creation of a linkage does not destroy biological activity; and 2) there must exist an "opening site" where new termini can be formed without disrupting a region critical for protein folding and desired biological activity. In some cases, such as streptavidin, it is desirable to modify biological activity, such as biotin binding in the case of streptavidin.

The Linker Between the Native Termini

Generally, linkers are molecules that contain two reactive sites, one which will form a covalent bond with the carboxyl terminal amino acid and one which will form a covalent bond with the amino terminal amino acid. Suitable linkers are well known to those of skill in the art and include, but are not limited to, straight or branched-chain carbon linkers, heterocyclic carbon linkers, or peptide linkers. The most common and simple example is a peptide linker that consists of several amino acids joined through the peptide bonds to the termini of the native protein. The linkers may be joined to the terminal amino acids through their side groups (e.g., through a disulfide linkage to cysteine). However, in a preferred embodiment, the linkers will be joined through peptide bonds to the alpha carbon amino and carboxyl groups of the terminal amino acids. The length of the linker is determined by the number of amino acids that make up the linker. Generally, neutral amino acids and/or amino acids with small side chains are preferred, such as glycine, alanine, and serine.

It is preferable to use a linker that preserves the spacing between the termini comparable to the unpermuted or native molecule, particularly if the desire is to maintain or improve the native biological activity of the molecule. In cases where this is not as important, the length or properties of the linker may not be as important. The length and properties of the linker are probably also more important when the termini to be linked are located near the active site.

For circularly permuted streptavidin, the linker is preferably about one to six amino acids. Most preferably, the linker is a tetrapeptide of three glycine residues and one serine residue, in the order Gly-Gly-Gly-Ser (SEQ ID NO:2). The first glycine is attached to the carboxyl terminal amino acid Ser139 (SEQ ID NO:1) of the native protein and the serine is attached to the amino terminal amino acid Ala13 (SEQ ID NO:1) of the native protein.

While the preferred embodiment is described herein as derived from wild type streptavidin, it should be apparent to those of skill in the art that the circular permutants and fusion proteins described herein can be made with variations of wild type streptavidin such as streptavidin mutants. The disclosed circularly permuted proteins based on circular permutation of streptavidin (including wild type, mutant, or variants) can be referred to as circularly permuted biotin binding proteins or circularly permuted streptavidin. Unless otherwise indicated or unless otherwise clear from the context, the term streptavidin is intended to encompass all forms of streptavidin including wild type streptavidin, mutant forms of streptavidin, or variants of streptavidin.

The Opening Site

The selection of an opening site may be determined by a number of factors. One factor is whether the biological function is to be preserved or altered. If the biological function is to be altered, the opening site should be away from the active site and away from other structure or functionally important sites. For example, preferred opening sites will be located in regions that do not show a highly regular three-dimensional structure such as alpha helices, pleated sheets, β barrel structures, and the like. However, if the object is to alter the biological function, it may be more advantageous to open the molecule near the active site. For example, to lower the biotin binding affinity of streptavidin, the opening site can be located on the flexible loop near the biotin binding site that contains amino acids that participate in biotin binding. This loop includes amino acids 45 through 52 (SEQ ID NO:1). In a preferred embodiment, residues 47–50 are removed from the loop (residues 1–4 of SEQ ID NO:3).

2. Design of the Fusion Protein

The fusion proteins described herein include a circularly permuted polypeptide (the base polypeptide) joined to another polypeptide (the secondary polypeptide). The two proteins may be fused together directly or joined by means of a spacer, such as a peptide spacer. The peptide spacer may range from about 1 to 40 residues in length. It is desirable to retain full or partial biological activity of both the base polypeptide and the secondary polypeptide. The length and characteristics of the spacer will be important in achieving this objective. Generally, the fusion protein can be produced by methods known to those of skill in the art for other fusion proteins. For example, the methods taught in U.S. Pat. No. 4,839,293 to Cantor et al. and U.S. Pat. No. 5,328,985 to Sano et al. for fusion of polypeptides to native streptavidin can be used.

The Secondary Polypeptide

The secondary polypeptide can be any polypeptide, and is preferably one having biological function such as an antibody, an antibody fragment, IBG-binding protein A, a hormone, an enzyme, a releasing factor, a ligand, a growth factor, a receptor such as the LDL receptor, or metallothionein. The secondary polypeptide can also be a portion of one of these or another protein that is sufficient to provide the biological activity desired.

The secondary protein can be purified as known in the art and attached chemically to the base polypeptide, as described further below. The secondary protein can alternatively be made from a fused polynucleotide that includes a polynucleotide for the base polypeptide and a polynucleotide for the secondary polypeptide. Means of fusing antibodies to circularly permuted proteins are well known to those of skill in the art. See, for example, Batra et al., Mol. Cell. Biol. 11:200–2205 (1991), Chaudhary et al., Nature 339: 394–397 (1989); Chaudhary et al. Proc. Natl. Acad. Sci. USA 87: 1066–1070 (1990); and Brinkmann et al., Proc. Natl. Acad. Sci. USA 88: 8616–8620 (1991).

The antibody component of the fusion protein may specifically bind antigens characteristic of certain types of cells such as cancer or virally infected cells. The antibodies used in the fusion protein can include various forms of modified or altered antibodies, such as an intact immunoglobulin, an Fv fragment containing only the light and/or heavy chain variable regions, an Fv fragment linked by a disulfide bond, an Fab or (Fab)'$_2$ fragment containing the variable regions and parts of the constant regions, a single-chain antibody, or a single domain of an antibody. The antibody may be of animal (especially mouse or rat) or human origin or may be chimeric or humanized. Methods of producing antibodies are well known to those skilled in the art and can be found described in such publications as Harlow & Lane, Antibodies: A Laboratory Manual, Cold Spring Harbor Laboratory (1988), and Asai, Methods in Cell Biology Vol. 37: Antibodies in Cell Biology, Academic Press, Inc. New York (1993).

The Spacer

Generally, the spacer connecting the base polypeptide to the secondary polypeptide has no biological activity itself and functions only to link and provide some distance between the two active proteins forming the fusion protein. However, one of skill will recognize that the residues of the spacer may be chosen to optimize a property of the fusion protein. For example, a spacer containing hydrophilic amino acids may enhance solubility in aqueous solutions. Similar, the spacer residues may be chosen for their effect on the folding of the fusion protein.

3. Methods of Making the Circularly Permuted Polypeptide and Fusion Protein

The circularly permuted proteins and fusion proteins may be made using methods known to those of skill in the art. These include chemical synthesis, modifications of existing proteins, and expression of circularly permuted proteins using recombinant DNA methodology. The fusion protein can be made as a single polypeptide or the second peptide can be attached to the base polypeptide after separate synthesis of the two component polypeptides.

Where the protein is relatively short (i.e. less than about 50 amino acids) the circularly permuted polypeptide and/or fusion protein may be synthesized using standard chemical peptide synthesis techniques. If the linker and/or spacer is a peptide it may be incorporated during the synthesis. If the linker is not a peptide it may be coupled to the peptide after synthesis. Similarly, the spacer may be incorporated to link the base and secondary polypeptides after they are generated independently. Solid phase synthesis in which the C-terminal amino acid of the sequence is attached to an insoluble support followed by sequential additional of the remaining amino acids in the sequence is the preferred method for the chemical synthesis of the circularly permuted ligands and fusion proteins described herein. Chemical synthesis produces a single stranded oligonucleotide. This may be converted into a double stranded DNA by hybridization with a complementary sequence, or by polymerization with a DNA polymerase using the single strand as a template. One of skill would recognize that while current methods for chemical synthesis of DNA are limited to preparing sequences of about 100 bases, longer sequences may be obtained by the ligation of shorter sequences. Techniques for solid phase synthesis are described by Barany and Merrifield, Solid-Phase Peptide Synthesis; pp.

3–284 in The Peptides; Analysis, Synthesis, Biology Vol. 2. Special Methods in Peptide Synthesis, Part A, Merrifield, et al., J. Am. Chem. Soc. 85: 2149–2156 (1963), and Stewart et al., Solid Phase Peptide Synthesis, 2nd ed. Pierce Chem. Co., Rockford, Ill. (1984).

Alternatively, the circularly permuted protein and/or fusion protein may be made by chemically modifying a native or preexisting protein. Generally, this requires reacting the native protein in the presence of the linker to form covalent bonds between the linker and the carboxyl and amino termini of the protein, thus forming a circular protein. New termini are then formed by opening the peptide bond joining amino acids at another location. This may be accomplished chemically or enzymatically using, for example, a peptidase.

If the opening reaction tends to hydrolyze more than one peptide bond, the reaction is run briefly. Those molecules having more than one peptide bond opened will be shorter than the full length circularly permuted molecule. These can be isolated by any protein purification technique that selects the size (e.g. by size exclusion chromatography or electrophoresis). Alternatively, various sites in the circular protein may be protected from hydrolysis by chemical modification of the amino acid side chains which may interfere with enzyme binding, or by chemical blocking of the vulnerable groups participating in the peptide bond.

In the preferred embodiment, the circularly permuted proteins, and/or fusion proteins including the circularly permuted protein, will be synthesized using recombinant methodology. Generally, this involves creating a polynucleotide sequence that encodes the circularly permuted base polypeptide (or the entire fusion protein containing the base polypeptide), placing the polynucleotide in an expression cassette under the control of a suitable expression promoter, expressing the protein in a host, isolating the expressed protein and, if required, renaturing the protein. If the secondary protein is made separately it is then ligated to the circular permutant.

DNA encoding a circularly permuted polypeptide or fusion protein including the circularly permuted polypeptide can be prepared by any suitable method, including, for example, cloning and restriction of appropriate sequences or direct chemical synthesis by methods such as the phosphotriester method of Narang et al. Meth. Enzymol. 68: 90–99 (1979); the phosphodiester method of Brown et al., Meth. Enzymol. 68: 109–151 (1979); the diethylphosphoramidite method of Beaucage et al., Tetra. Lett., 22: 1859–1862 (1981); and the solid support method of U.S. Pat. No. 4,458,066.

Alternatively, partial length sequences may be cloned and the appropriate partial length sequences cleaved using appropriate restriction enzymes. The fragments may then be ligated to produce the desired DNA sequence.

In a preferred embodiment, DNA encoding the circularly permuted polypeptide will be produced using DNA amplification methods, for example polymerase chain reaction (PCR).

The circularly permuted ligands and their fusion proteins may be expressed in a variety of host cells, including E coli, other bacterial hosts, yeast, and various higher eukaryotic cells, such as the COS, CHO and HeLa cells lines, insect cells, and myeloma cell lines. In a preferred embodiment, the fusion protein is encoded by a plasmid or a viral vector. The recombinant protein gene is operable linked to appropriate expression control sequences for each host. For expression in *E. coli* the plasmid should include a promoter such as the T7, trp, or lambda promoters, and a ribosome binding site. For expression in eukaryotic cells the vector preferably includes a promoter appropriate for the host cells, an enhancer, for example, derived from immunoglobulin genes, SV40, or cytomegalovirus, and a polyadenylation sequence, and may include splice donor and acceptor sequences.

The plasmids encoding the fusion protein can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes. Viral cells can be infected with vectors such as retroviral or adenoviral vectors.

Once expressed, the recombinant base circular permutant or fusion protein can be purified according to standard procedures of the art, including ammonium sulfate precipitation, affinity columns, column chromatography, gel electrophoresis and the like. Substantially pure compositions of at least about 90 to 95% homogeneity are preferred, and 98 to 99% or more homogeneity are most preferred for pharmaceutical uses. Once purified, partially or to homogeneity as desired, the polypeptides may then be used as desired.

One of skill in the art would recognize that after chemical synthesis, biological expression, or purification, the circularly permuted polypeptide and/or fusion protein may possess a conformation substantially different than the native protein. In this case, it may be necessary to denature and reduce the protein and then to cause the protein to re-fold into the preferred conformation. Methods of reducing and denaturing the protein and inducing re-folding are well known to those of skill in the art. For example, the expressed, purified protein may be denatured in urea or guanidium chloride and renatured by slow dialysis.

To determine which circularly permuted polypeptides or fusion proteins are preferred, the proteins should be assayed for biological activity. Such assays, well known to those of skill in the art, generally fall into two categories; those that measure the binding affinity of the protein to a particular target, and those that measure the biological activity of the protein.

4. Methods of Using the Circularly Permuted Polypeptides and Fusion Proteins

The circularly permuted polypeptides are useful for creating fusion proteins. For example, circularly permuted streptavidin can be used to create fusion proteins that are more useful because they do not bind to biotin as tightly as prior fusion proteins.

The fusion proteins are useful for a variety of applications such as separations, drug delivery, targeting, and in diagnostic assays. For example, a streptavidin fusion protein can be bound to a biotinylated substrate. The biological activity of the secondary molecule can then be used, for example, to capture and separate a particular molecule out of an impure solution. The purified molecule is then dissociated from the fusion protein. The lower biotin affinity of the fusion protein as compared to that of the wild type streptavidin allows release of the fusion protein from the substrate and reuse of the fusion protein. The two prong specificity of the fusion protein can be used similarly in other applications.

The present invention is further described by the following non-limiting example.

EXAMPLE

Preparation and Characterization of a Circularly Permuted Streptavidin

A circularly permuted streptavidin, designated CP51/46, was prepared. The original termini (residues 13 and 139' of SEQ ID NO:1) were joined by a tetrapeptide linker (GGGS) (SEQ ID NO:2). Four of the loop residues (47–50) SEQ ID NO:1) were removed, resulting in the creation of new N-and C-termini at Glu51 and Ala46 (residues Glu2 and Ala 128 of SEQ ID NO:4). The initiating methionine was not removed by post-translational processing and became the new N-terminus (Met1 of SEQ ID NO:4) rather than Glu51 (Glu 2 of SEQ ID NO:4).

Materials and Characterization Methods

Unless otherwise noted, all oligonucleotides were obtained from Integrated DNA Technologies (Coralville, Iowa), plasmids and cells were from Novagen (Madison, Wis.), PCR reagents were obtained from Promega (Madison, Wis.), restriction enzymes and ligases were supplied by New England Biolabs (Beverly, Mass.), and chemical reagents were obtained from Sigma (St. Louis, Mo.).

N-terminal sequencing was performed on an Applied Biosystems Model 477A Sequencer. SDS/PAGE analysis was done using precast Mini-Protean 10–20% gradient gels (Bio-Rad, Hercules, Calif.). The concentration of CP51/46 was determined by absorption at 280 nm using an extinction coefficient ($\epsilon_{280}$) of 34000 $M^{-1}cm^{-1}$ for the subunit (Sano T, et al. (1990) Proc Natl Acad Sci USA 87:142–146). Electrospray mass spectrometry was performed on a VG Quattro II Tandem Quadrupole Mass Spectrometer.

Construction of the circularly permuted gene

The circularly permuted variant was constructed from a synthetic gene for core streptavidin as taught by (Chilkoti A, et al. (1995) Proc Natl Acad Sci USA 92:1754–1758). A Gly-Gly-Gly-Ser linker (SEQ ID NO:2) was used to connect the original termini. A tandem gene (Horlick R A, et al. (1992) Protein Eng 5:427–431) of streptavidin was constructed first to serve as a "template" for the generation of desired circular permutations. The tandem streptavidin gene was constructed in two halves from the wild-type gene using PCR mutagenesis. Four primers were used pairwise to generate each half. The first half codes for the wild-type gene with a new linker sequence appended to the 3' end. This linker sequence codes for the Gly-Gly-Gly-Ser segment which bridges the original termini of streptavidin. The second half attaches the linker sequence to the 5' end of the streptavidin gene. Both fragments were generated in separate PCR reactions and subcloned into pT7Blue plasmids. After cutting with the NheI restriction enzyme at a unique site in the linker region of both fragments, the two halves were ligated together to create the tandem streptavidin gene. The sequences of each set of fragments as well as that of the final assembly were checked for errors using dye-terminated DNA sequencing.

To create the CP51/46 mutant through PCR mutagenesis, two additional primers were designed and synthesized. The sense primer anneals at residue 51 in the first half of the tandem gene and adds an NdeI site to the beginning of the gene. The antisense primer anneals at residue 46 in the second half of the tandem gene and adds stop codons followed by a HindIII site. Thirty-five cycles of PCR mutagenesis (90° C.×2 min; 50° C.×2 min; 72° C.×2 min) produced the circularly permuted gene which was ligated into Novagen (Madison, Wis.) pT7Blue plasmids and transformed into NovaBlue maintenance hosts. The gene was later subcloned into Novagen pET-21a plasmids in BL21 (DE3) hosts for expression. The name, CP51/46, reflects the relocation of the N-terminus to residue 51 of the original wild-type sequence and relocation of the C-terminus to residue 46. DNA sequencing was used to confirm the integrity of the mutant gene.

Expression of CP51/46 in *E. coli*

BL21(DE3) cells containing the CP51/46 gene in pET-21a were cultured overnight at 37° C. in Luria-Bertani (LB) media. The cell pellet was washed and re-suspended in fresh LB before being used to inoculate 5 liters of 2×YT media supplemented with 100 µg/mL ampicillin. The culture was incubated at 37° C. with shaking until the A600 reached 1.0, when protein expression was induced by the addition of 1 mM isopropyl-β-D-thiogalactoside (IPTG). Cells were cultured for an additional three hours before harvesting by centrifugation.

Isolation and Purification of CP51/46

Cell pellets were re-suspended in 50 mM Tris-HCl, 200 mM NaCl, 5 mM EDTA, 8% sucrose, 1% Triton X-100, and 1 mM phenylmethylsulfonyl fluoride (PMSF) at pH 8.0. Cells were lysed by sonication and centrifuged at 17700 g for 20 minutes. The insoluble fraction was sonicated and centrifuged twice more and pellets were then sonicated and centrifuged three times in the same buffer without Triton X-100. The remaining insoluble inclusion bodies containing the CP51/46 protein were dissolved in 6 M guanidine, 50 mM Tris-HCl at pH 7.5 to a concentration of no more than 10 mg/mL and allowed to equilibrate for several hours at 4° C. Solubilized protein was then diluted dropwise with stirring at 4° C. in a 50× volume of 50 mM Tris-HCl, 100 mM NaCl, 5 mM EDTA, 0.1 mM PMSF at pH 7.5 and allowed to equilibrate overnight. The resulting solution was centrifuged to remove insoluble material and concentrated in a stirred Amicon (Beverly, Mass.) ultrafiltration cell.

CP51/46 was purified by affinity chromatography over Pierce (Rockford, Ill.) iminobiotin-agarose (Hofmann, Wood, Brinton, Montibeller & Finn, 1980). Protein-containing fractions were pooled and exchanged into a storage buffer of 50 mM phosphate, 100 mM NaCl at pH 7.75.

Isothermal Titration Calorimetry

Isothermal titration calorimetry (ITC) experiments on wild-type streptavidin were performed on a MicroCal Omega instrument. ITC experiments on CP51/46 were done using a Calorimetry Science Corporation 4200 Calorimeter (Provo, Utah). CP51/46 solutions of 30–40 µM concentration were titrated by the addition of 20×5µL aliquots of 750 µM biotin dissolved in the same buffer as the protein. All ITC experiments were done in either phosphate (50 mM sodium phosphate, 100 mM NaCl, pH 7.75) or Tris (50 mM Tris HCl, 100 mM NaCl, pH 7.75) buffers. Biotin concentrations were determined gravimetrically.

Data were analyzed using the proprietary software supplied by Calorimetry Science Corporation with the instrument. Heats of dilution for each injection were subtracted from the reaction heats before data analysis. Nonlinear fitting of the data allowed the number of binding sites (n), association constant ($K_a$), and binding enthalpy ($\Delta H°$) to be determined assuming noncooperative binding and one site per subunit.

Figure 1:
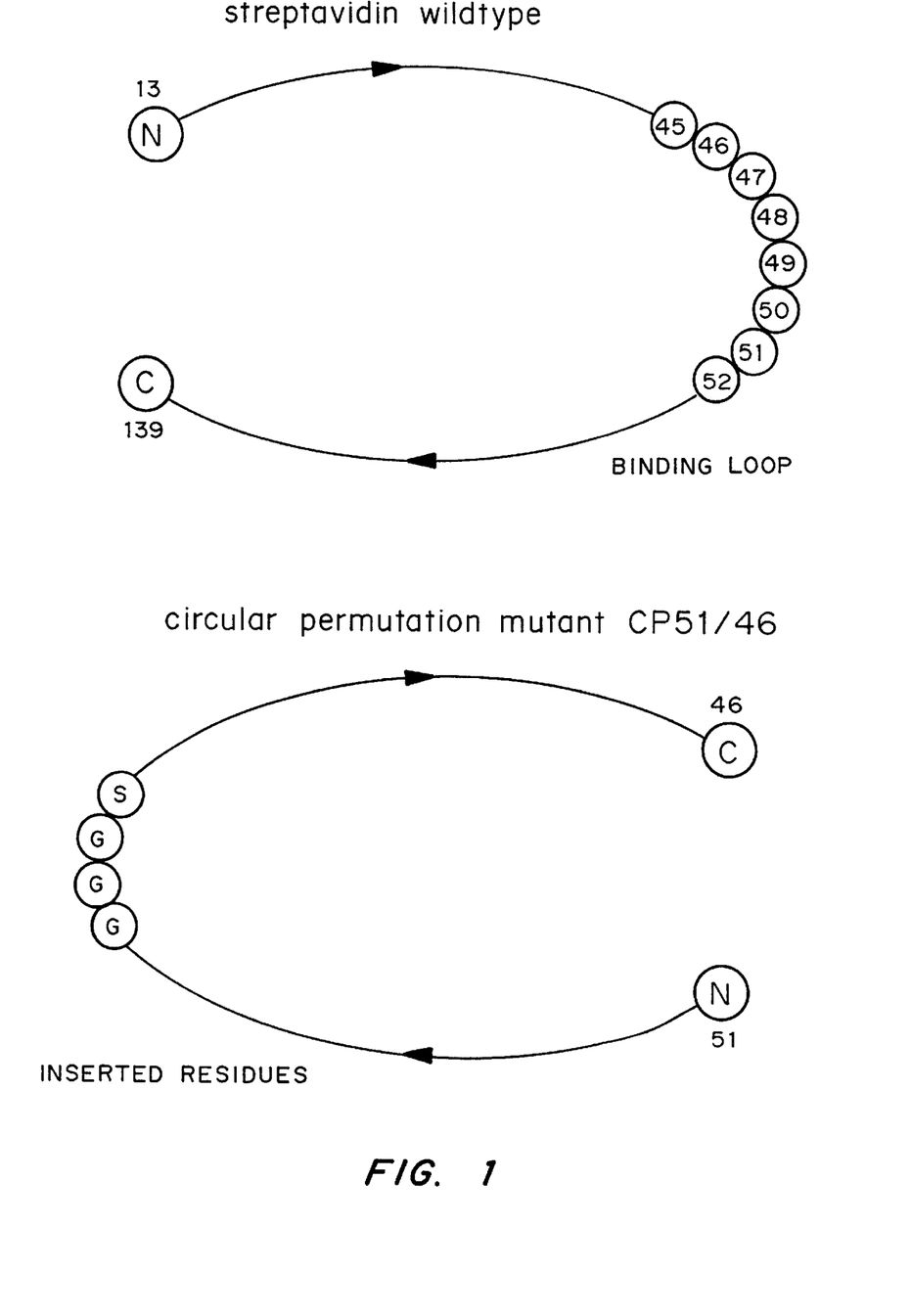
FIG. 1 is a schematic showing the relationship between the amino acid sequences of wild-type core streptavidin and a preferred embodiment of the circularly permuted streptavidin, designated CP51/46. Loop residues 47 through 50 of the wild type protein (SEQ ID NO:1) have been removed, and the old N- and C-termini have been joined by a four amino acid residue linker (residues 1–4 of SEQ ID NO:2).
Figure 2A:
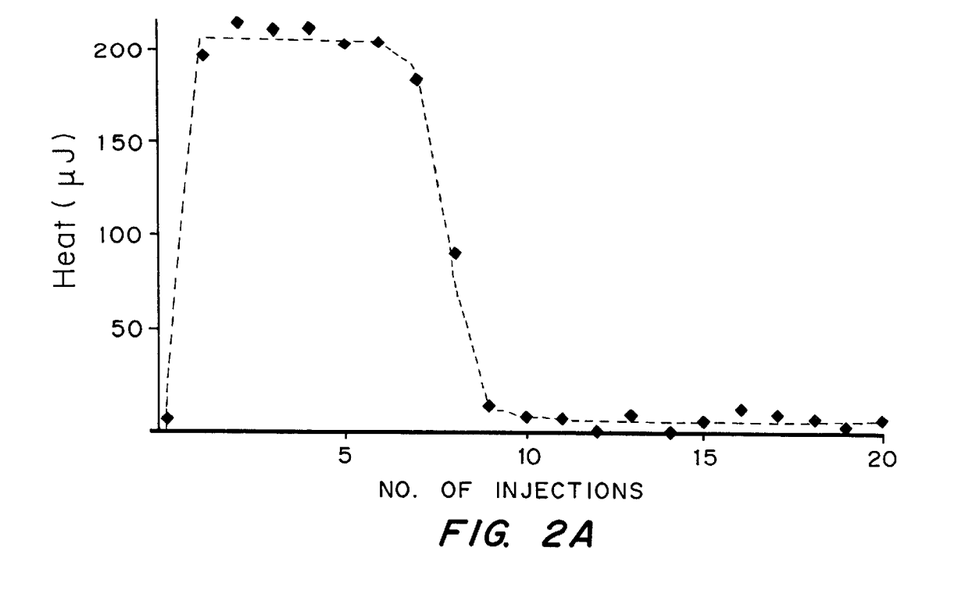
FIG. 2A is a graph of injections versus heat (in $\mu J$), illustrating a typical binding isotherm for CP51/46 at 25° C. Heats for each injection are shown as solid symbols (♦) and have been adjusted for heat of mixing. Parameterized fit is shown as a dotted line.

Wild-type streptavidin displays a $K_a$ that has been estimated to be $2.5 \times 10^{13}$ $M^{-1}$ (Green N M (1990). Avidin and streptavidin, Methods Enzymol 184:51–67), and the standard binding enthalpy of wild type streptavidin is −24.9 kcal/mol at 25° C. (Chilkoti A, et al. (1995) J Am Chem Soc 117:10622–10628). Using the estimated $K_a$ and associated standard Gibb's free energy, the T$\Delta$S° term for wild-type streptavidin would then be −6.6 kcal/mol at 25° C. With the CP51/46 mutant, the $K_a$ for biotin is reduced approximately six orders of magnitude to 2.28 (±0.44)×10⁷ $M^{-1}$ ($\Delta G°$=−10.0 kcal/mol) at 25° C. (see FIG. 2a). The association of biotin is still enthalpically driven with a $\Delta H°$ of −13.8 (±0.8)

kcal/mol and the $T\Delta S°$ term is $-3.8$ ($\pm 0.8$) kcal/mol at 25° C. The enthalpy values in both phosphate and Tris buffers are within experimental error of each other, suggesting that protonation effects are not significant in the mutant (see Table 1 below).

Figure 2B:
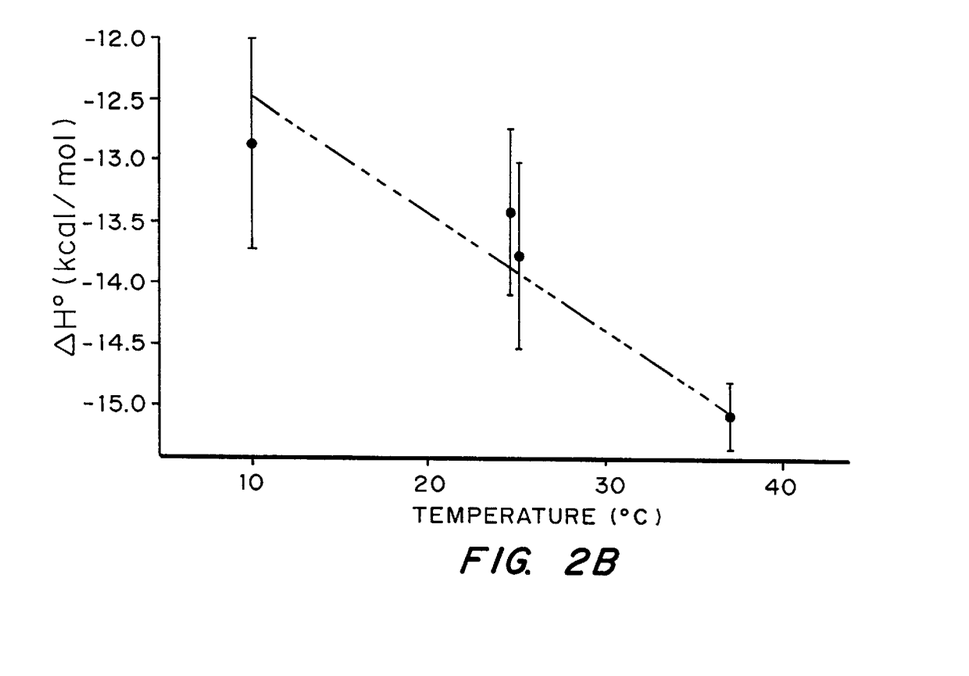
FIG. 2B is a graph of the change in enthalpy ($\Delta H$, in kcal/mol) versus temperature (T, in ° C.) showing the linear fit for the change in heat capacity ($\Delta C_p$) of CP51/46. Solid symbols (•) represent average change in standard enthalpy ($\Delta H°$) for three experiments. Error bars indicate one standard deviation. The dotted line represents the linear fit of data.

The change in heat capacity was also measured for CP51/46 to provide further thermodynamic insight into the role of the loop (see FIG. 2b). The $\Delta C_p$ was significantly less negative ($-95$ cal/mol° C. (standard deviation=29 cal/mol° C.)) compared to the value for wild-type streptavidin ($-345$ cal/mol° C. (standard deviation=12 cal/mol° C.)). This alteration is qualitatively consistent with the expected decrease in surface area buried in the CP51/46 bound state after loop deletion. Previous analysis of the avidin-biotin system by Spolar R S, et al. (1994) Science 263:777–784 suggested that $\Delta C_p$ for biotin association is dominated by the folding of the loop residues. The results of calculations relating to $\Delta C_p$ and changes in the accessible surface area are presented in Table 1b.

the mutant streptavidin from hanging drop experiments. The protein solution was 12 mg/mL in CP51/46, 10 mM biotin. The reservoir solution was 52% MPD. The crystals were long plates with dimensions 0.1×0.3×0.7 mm. Diffraction data were collected at beamline 9-1 at the Stanford Synchrotron Radiation Laboratory at 100 K ($\lambda$=0.98 Å). Earlier attempts to collect room temperature data on an R-AXIS II resulted in lower resolution data sets (2.3 and 2.6 Å). The shock frozen crystal diffracted to 1.8 Å resolution with a mean I/σ of 15.8. The overall completeness of the data set is 98%. The unit cell parameters are a=71.9 Å, b=78.6 Å, c=90.8 Å. The orthorhombic space group is $P2_12_12_1$. One tetramer of the protein-biotin complex is in the asymmetric unit in this crystal form. The data processing and scaling were carried out using DENZO and SCALEPACK (Otwinowski Z, et al. (1994). DENZO: A film processing program for macromolecular crystallography. New Haven. Conn.: Yale University). The overall $R(I)_{merge}$ was 0.037 (Table 2).

TABLE 1a

Thermodynamic comparison of wild-type and CP51/46 streptavidin

| Protein | $K_a$ (M$^{-1}$) | $\Delta G°$ (kcal/mol) | $\Delta H°$ (kcal/mol) | $T\Delta S°$ (kcal/mol) | $\Delta C_p$ (kcal/mol°C.) |
|---|---|---|---|---|---|
| wild-type | $2.5 \times 10^{13}$ | $-18$ | $-24.9 \pm 0.4$ | $-6.6 \pm 0.4$ | $-345 \pm 12$ |
| CP51/46 (PB) | $(2.28 \pm 0.44) \times 10^7$ | $-10.0$ | $-13.8 \pm 0.8$ | $-3.8 \pm 0.8$ | $-95 \pm 29$ |
| CP51/46 (Tris) | $(2.47 \pm 1.87) \times 10^7$ | $-10.1$ | $-13.4 \pm 0.7$ | $-3.3 \pm 0.7$ | — |

(Values reported are per mol of subunits)

TABLE 1b

Comparison of Observed and Calculated Values of $\Delta C_p$

| | wild-type | | CP51/46 | |
|---|---|---|---|---|
| | calculated | observed | calculated | observed |
| Δ accessible surface (apolar) (Å$^2$) | $-566$ | — | $-446$ | — |
| Δ accessible surface (polar) (Å$^2$) | $-146$ | — | $-234$ | — |
| Δ Cp (cal/mol° C.) | $-216$ | $-345$ | $-139$ | $-95$ |

(Surface areas reported are for an average subunit in the tetramer.)

Crystallization and Diffraction Data Collection

A CP51/46 protein solution with a concentration of 30 mg/mL in water used for crystallization experiments (hanging drop vapor diffusion method). The mutant crystallized in the form of rods from solutions containing 52% MPD (2-methyl-pentane-2,4-diol). A crystal with dimensions of 0.05×0.05×0.5 mm was mounted in a glass capillary, and diffraction data were collected on an R-AXIS II image plate detector system attached to a Rigaku RU-200 rotating anode (CuKα,=1.54178 Å) at 293 K. The crystal diffracted to 2.0 Å resolution, and data were collected to a completeness of 94% with a mean I/σ of 5.2. The orthorhombic unit cell dimensions area a=60.3, b=78.6, c=93.5 Å, and the space group is $P2_12_12_1$ (Z=4). One tetramer of the protein is found in the asymmetric unit. Data processing was carried out using DENZO (Otwinowski Z, et al. (1994). DENZO: A film processing program for macromolecular crystallography. New Haven. Conn.: Yale University). The overall $R(I)_{merge}$ was 0.069. Table 2 below gives an overview of the collected data. Crystals of the biotin complex of CP51/46 were obtained by co-crystallization of biotin and

TABLE 2

X-ray data for streptavidin CP51/46 and its biotin complex

| Parameter | CP51/46 | CP51/46 + biotin |
|---|---|---|
| Space group | $P2_12_12_1$ | $P2_12_12_1$ |
| Unit cell parameters a (Å) | 60.3 | 71.9 |
| b (Å) | 78.6 | 78.6 |
| c (Å) | 93.5 | 90.8 |
| Number of tetramers (subunits) per unit cell | 4(16) | 4(16) |
| Packing parameter $V_M$ (Å$^3$/Da) | 2.1 | 2.4 |
| Resolution (Å) | 2.0 | 1.8 |
| Wavelength (Å) | 1.54178 | 0.980 |
| Measured reflections | 28795 | 52691 |
| Completeness, overall (%) | 94.4 | 98.2 |
| outermost shell (%) | 82.1 | 96.2 |
| $R_{merge}$ overall | 0.05 | 0.03 |
| outermost shell | 0.32 | 0.17 |

Structure Solution and Refinement

A tetrameric wild-type core-streptavidin model (residues 16 to 44 and 52 to 133, PDB. entry 1SWA, (Freitag S, et al. (1997) Protein Sci 6:1157–1166) was employed as a search model in the molecular replacement structure solution for CP51/46 using X-PLOR (Brünger A T (1992) X-PLOR, A System for Crystallography and NMR, v.3.1. Yale University Press, New Haven, Conn.). After application of the results of a cross-rotation function and a translation function, the R-value was 0.457. The two-fold symmetry axes of the tetramer were not aligned with the crystallographic axes, confirming the existence of a tetramer in the asymmetric unit.

The resulting model was subjected to full matrix, least squares rigid body refinement with the β-test version of SHELXL-97 (Sheldrick G M (1997) SHELXL, Program for Structure Refinement. Göttingen: University of Göttingen), giving R=0.384 for data with I>2σ(I). Throughout the refinement, all data were included from 10 Å resolution to the highest limit (2.0 Å). 10% of the reflection data were held in a separate file and used for calculation of $R_{free}$ (Brünger A T (1992) Nature 355:472–475). At this stage the value of $R_{free}$ (I>2σ(I)) was 0.422. Subsequent positional and B-factor refinement using conjugate gradient methods (Konnert J H, et al. (1980) Acta Crystallogr A36:344–350) as implemented in SHELXL lowered the R-value (I>2σ(I)) to 0.265 and $R_{free}$ (I>2σ(I)) to 0.335. Electron density for the new engineered loop (residues 133 to 18) was observed in subunits 2 and 3 in $|F_0|F-|F_c$ maps after the first refinement steps. The modeling of these two loops and addition of 31 water positions in the refinement decreased the R-value to 0.213 and $R_{free}$ to 0.300 (both for data with I>2σ(I)). The final model contains residues 52 to 133 and 143 to 145 in subunits 1 and 4, and residues 52 to 45 in subunits 2 and 3, as well as 214 water molecules. The final R-value (I>2σ(I)) is 0.145 (0.195 for all data) and $R_{free}$ (I>2σ(I)) is 0.229 (0.288 for all data).

Molecular replacement methods were again used to solve the structure of the biotin complex, starting with the same wild-type streptavidin model. The AMoRe program package (Navaza J (1994) Acta Crystallogr A50:157–163) was employed for the solution, and the correlation coefficient for the best solution from the rotation function was 0.298. The best solution after calculating the translation function for the eight best rotation solutions had a correlation coefficient of 0.523 and an R-value of 0.411. After rigid body refinement for the complete tetramer and for all four subunits separately, coordinate refinement with SHELXL-97 (Sheldrick GM (1997) SHELXL, Program for Structure Refinement. Göttingen: University of Göttingen) resulted in an R-value of 0.412 for data with I>2σ(I) and an $R_{free}$-value of 0.442. All data in the range from 10 to 1.8 Å resolution were used throughout the refinement, as described above for the unbound structure. The $F_{free}$ data set contained 10% of the data in the range. Biotin was clearly identified in the binding sites of all four subunits in the Sigma A weighted $|F_o|-|F_c|$ electron density maps (Read R J (1986) Acta Crystallogr A42: 140–149). Also, in subunit 3, the residues for the engineered loop were modeled in a conformation differing from that in the unbound structure. The final model for the biotin complex includes residues 52 to 132 and residues 16 to 46 in subunits 1 and 2; residues 52 to 46 in subunit 3 and residues 51 to 133 and 16 to 45 in subunit 4; as well as four biotin ligands and 335 water molecules. The final R-value is 0.181 for data with I>2σ(I) and 0.192 for all data. The final $R_{free}$-values are 0.231 (I>2σ(I)) and 0.245 (all data).

Both molecular models were refined against the squares of the structure factor amplitudes. All parameters, coordinates and isotropic displacement parameters were refined together. Target values for 1,2- and 1,3-distance restraints were based on the study of Engh R A, et al. (1991) Acta Crystallogr A47:392–400. Planarity and chiral volume restraints were applied as were similarity restraints for the isotropic displacement parameters and anti-bumping restraints if non-binding atoms came closer than a target distance. Diffuse solvent regions were modeled using Babinet's principle (Moews P C, et al. (1975) J Mol Biol 91:201–228). Anisotropic scaling of the observed structure factors (Parkin S, et al. (1995) J Appl Crystallogr 28:53–56) as implemented in SHELXL was applied in the refinements. Hydrogen atoms were geometrically idealized and refined with a riding model in the last cycles.

Figure 3:
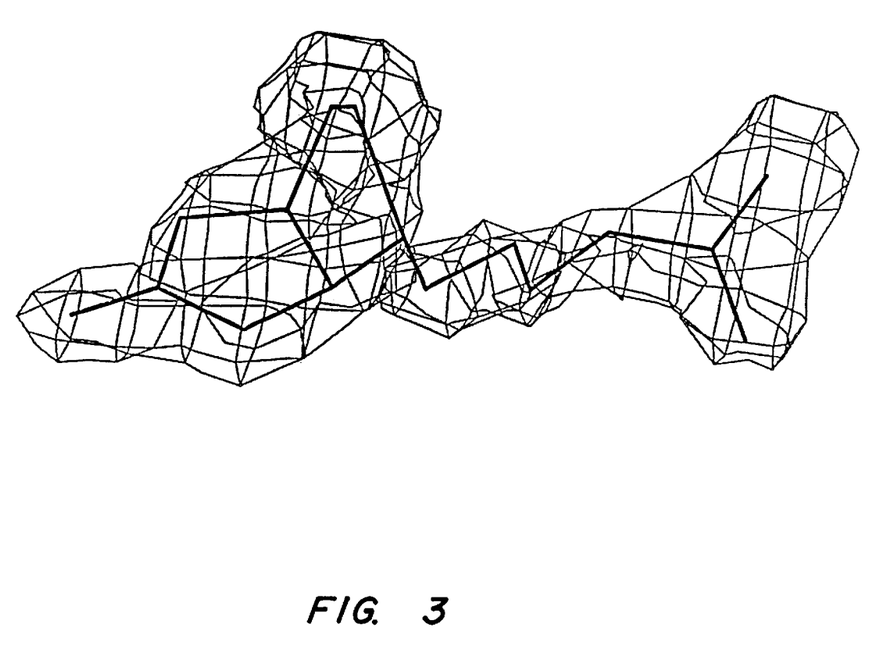
FIG. 3 is an unbiased electron difference map contoured at 2.4 σ in the region of biotin in one of the subunits in the circularly permuted streptavidin-biotin complex. Superimposed is the refined biotin.
Figure 4A:
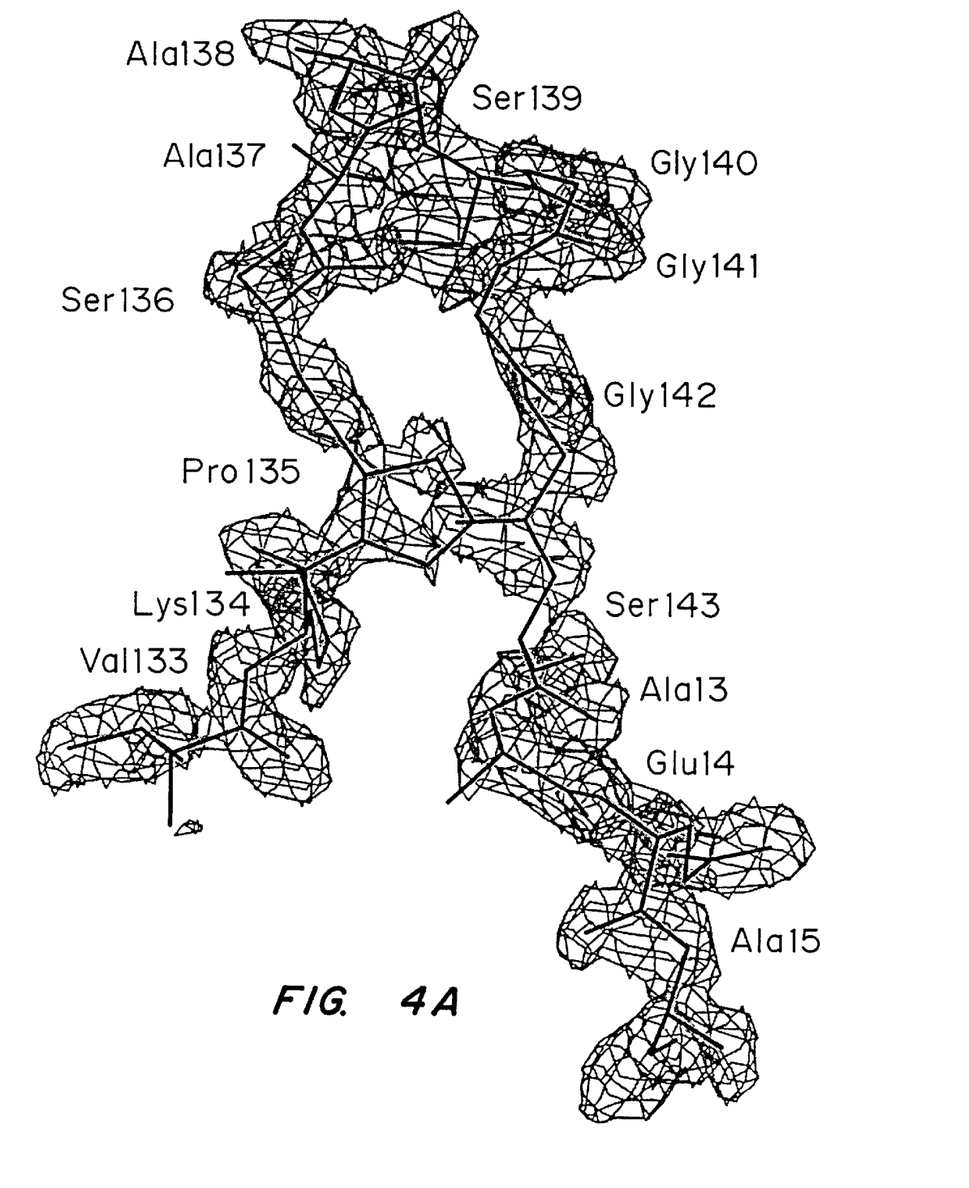
FIGS. 4A and 4B are electron density maps in the region of the new engineered connecting loop (including residues 133 to 15) as observed in subunit 2 and 3 of the CP51/46 structure (contoured at 1.5 σ)(FIG. 4A) and subunit 3 of the CP51/46 mutant-biotin complex (1.5 σcontour level)(FIG. 4B).
Figure 4B:
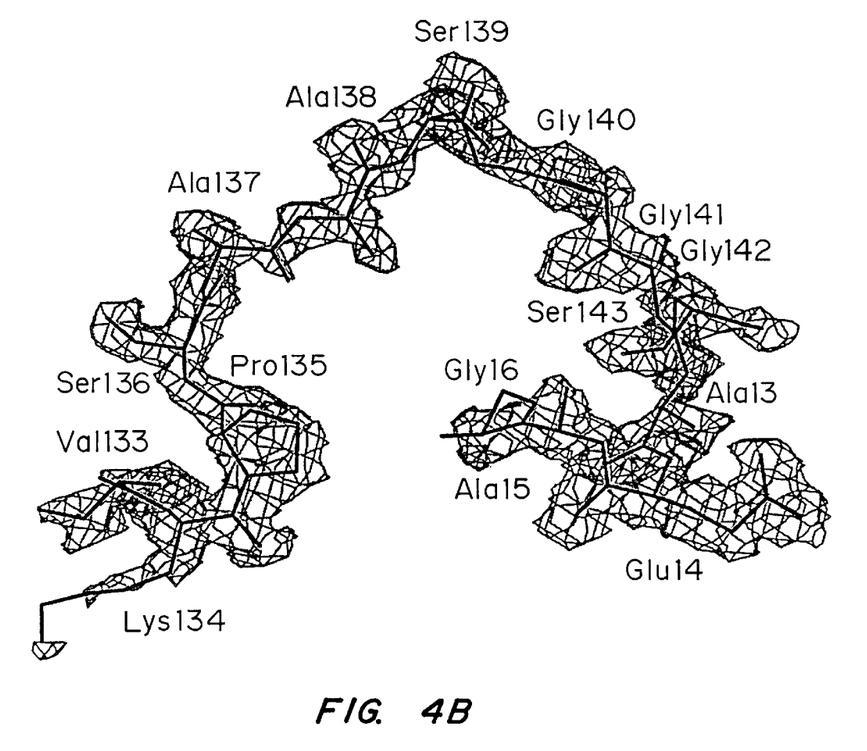
Figure 5:
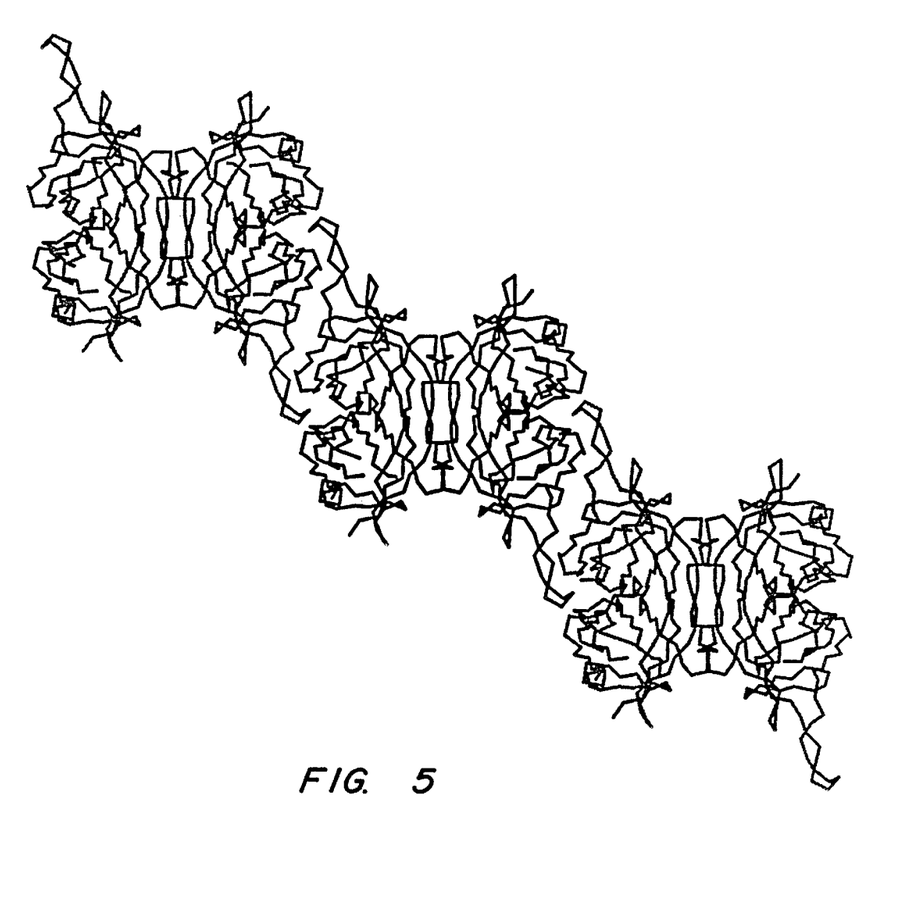
FIG. 5 is a diagram illustrating the packing interactions between neighboring CP51/46 tetramers. The engineered loops of adjacent tetramers are highly involved in interactions with the next tetramer in the crystal.

XtalView (McRee D E (1992) J Mol Graph 10:44–46) was used for graphical evaluation of the model during the refinement. Sigma A weighted $|F_o|-|F_c|$ and $2|F_o|-|F_c|$ electron density maps (Read R J (1986) Acta Crystallogr A42:140–149) were calculated with the interactive interface program SHELXPRO (Sheldrick G M (1997) SHELXL, Program for Structure Refinement. Göttingen: University of Göttingen). In addition, the programs PROCHECK (Laskowski R A, et al. (1993) J Appl Crystallogr 26:283–291) and WHATIF (Vriend G, et al. (1993) J Appl Crystallogr 26:47–60) were employed to check the stereochemistry during the refinement process. Most of the refined water positions were found by SHELXWAT, an auxiliary program of SHELXL for automated water position searches. All root mean square deviations for least squares fits were calculated with X-PLOR using residues 19–23, 28–33, 38–42, 54–60, 71–80, 85–97, 103–112, 123–131 (SEQ ID NO:1) in the β sheet region. FIGS. 3, 4, and 5 are XtalView plots (McRee DE (1992) J Mol Graph 10:44–46).

The crystal structure of CP51/46 was determined at 2.0 Å resolution and refined to an R-value of 0.145. Results of the data collection and model refinement are summarized in Tables 2 and 3. Comparisons of the overall fold of the CP51/46 tetramer with other core-streptavidin structures indicate no major differences between them. Least squares fits of 4×65β-sheet Cα atoms of CP51/46 on the monoclinic wild-type structures (PDB entries 1 SWA, 1 SWB, 1SWC) result in rms distances RMSDs of 0.2 Å for the fitted subunit and values in the range of 0.2 to 1.0 Å for the other three subunits. Least squares superpositions of the four individual CP51/46 subunits on each other show no significant differences (TMSDs=0.2 Å, respectively), indicative of no systematic change in the β-barrel structure.

TABLE 3

Refinement statistics for streptavidin CP51/46 and its biotin complex

| protein | CP51/46 | CP51/46 + biotin |
|---|---|---|
| Resolution range (Å) | 10–2.0 | 10–1.8 |
| Unique reflections | 28548 | 42736 |
| Non-hydrogen atoms | 3576 | 3525 |
| Water molecules | 214 | 335 |
| R-factor[a] | 0.145 | 0.181 |
| Free R-factor[b] | 0.229 | 0.231 |
| Average B-factor[c] (Å$^2$) | 29 | 27 |
| Ramachandran quality[d] | 0.92 | 0.90 |

[a] for all data with F >4σ(F)
[b] for 10% of the data with F >4σ(F)
[c] for all atoms
[d] fraction of residues (except Gly and Pro) in 'most favored regions' (Laskowski RA, et al. (1993) J Appl Crystallogr 26:283–291).

The crystal structure of the biotin complex of CP51/46 was determined and refined at 1.8 Å resolution. The final R-value is 0.181. Electron density for biotin was clearly defined for all atoms in the small molecule ligand (FIG. 3). The RMSD after superposing 4×65 Cα atoms of the CP51/46-biotin complex on the wild-type biotin complex structure is 0.3 Å. Superposition of the wild-type tetrameric complex onto that of CP51/46, but based on superposition of only one subunit, gives RMSDs of 0.2 to 0.3 Å for the fitted subunit and 0.3 to 0.7 Å for the other three subunits.

Characterization of Connecting Residues

While the overall structure of apo-CP51/46 is the same as that of wild-type streptavidin, there are structural changes at the two regions where the protein was specifically altered. A feature of the unbound CP51/46 structure is the observation (in two of the four subunits in the crystal) of the ordered, engineered polypeptide connecting the old N- and C-termini. This part of the structure (including 17 residues) is well ordered in subunits 2 and 3. Difference electron density in this region is shown in FIG. 4(a). Residues 13 to 15 and 134 to 139 (SEQ ID NO:1) have been disordered in other monoclinic wild-type structures (Freitag S, et al. (1997) Protein Sci 6:1157–1166), but in the CP51/46 crystals, they can clearly be identified, along with the four inserted residues Gly140, Gly141, Gly142, and Ser143 (SEQ ID NO:1). The amino acid sequence of the connector between the old N- and C-termini is [ . . . Val133-Lys-Pro-Ser-Ala-Ala-Ser-Gly140-Gly- Gly-Ser143-Ala13-Glu-Ala-Gly16 . . . ] (residues Val84 through Gly108 of SEQ ID NO:4).

The two observed connectors (residues 133 to 16) (residues 84 to 108 in SEQ ID NO:4) form the regions of major packing interactions in this crystal form (FIG. 5). Two connectors from each tetramer form interactions with two neighboring tetramers, which also interact with one of their connecting regions with the first tetramer. The rigidity of the linking residues in subunit 2 and 3 compared to other loop regions in the protein can be explained by these packing interactions and is shown by their low temperature factors. The average B-values for the atoms of residues 133 to 18 (residues 84 to 110 in SEQ ID NO:4) in subunit 2 is 25 Å$^2$, in subunit 3, 24 Å$^2$ (average B-value for all atoms in the tetramer: 29 Å$^2$).

A Ramachandran plot for the CP51/46 structure including the engineered linkers shows no outliers, and the $\phi/\Psi$ distribution in these regions is normal. The connecting regions in subunits 2 and 3 are very similar. Superposition of the structures between the Cα atoms of residues 133 to 18 (residues 84 to 110 in SEQ ID NO:4) yields an RMSD of 0.16 Å. The program PROMOTIF (Hutchinson E G, et al. (1996) Protein Sci 5:212–200) finds no secondary structural elements other than a 3$_{10}$-helical portion formed by residues Ala137, Ala138 and Ser139 (residues Ala88, Ala89, Ser90 of SEQ ID NO:4). In the other subunits (1 and 4) only residues 143, 13, 14, and 15 (residues Ser94, Ala95, Glu96, Ala97 of SEQ ID NO:4) are observed in the electron density beyond those seen in the wild-type structures. Residues 13 to 17 (residues 95–99 in SEQ ID NO:4) were identified by PROMOTIF as forming an α-helix in both subunits. Superpositions of subunits 2 and 3 (where the complete connectors are observed) on subunits. Superpositions of subunits 2 and 3 (where the complete connectors are observed) on subunits 1 and 4 show that the rigid conformation for the linker would not fit in the crystal packing for the latter subunits. The connecting residues 134 to 142 (residues 85–93 of SEQ ID NO:4) are disordered in subunits 1 and 4. Because of the different orientation of the old C-terminal residues in CP51/46, the adjacent Tyr22 (Tyr104 in SEQ ID NO:4) side-chain adopts a conformation with χ1 rotated by about 180° in all four subunits. Other side chain changes were not detected in the unbound form.

The biotin complex of CP51/46 crystallizes in a different crystal form from that of the uncomplexed mutant, and the connecting polypeptide is ordered for only subunit 3 (FIG. 4(b)). The conformation of the linker differs from that seen in the unbound structure, and includes a short segment of α-helix (residues 14 to 17) (residues 96–99 in SEQ ID NO:4).

The ordered linker in the crystal structure of the biotin complex contacts a biotin molecule bound in subunit 2 of a neighboring tetramer. A hydrogen bond (3.0 Å) is formed between the amide nitrogen atom of Ser139 (Ser90 in SEQ ID NO:4) (of a symmetry related molecule) and one of the oxygens (O1) of the carboxyl group on the aliphatic chain of biotin. There are also two interactions between Ser 139 Oγ of the symmetry related molecule with both of the carboxyl oxygens (3.4 Å to O1 and 2.5 Å to O2). These are not sufficient to cause a conformational change in the biotin bound in this subunit, but the biotin temperature factors are lower in this subunit than in the others, consistent with the additional interactions between the ligand and the connecting loop.

Characterizations of the Binding Site in Apo-CP51/46 and the CP51/46-Biotin Complex Introduction of new N- and C-termini near the biotin binding site could significantly change the protein structure and thus its binding affinity for biotin. Three residues at the new N- and C-termini are disordered in the unbound structure and unobserved in electron density maps. The N-terminal methionine is not seen in the electron density. Residue Glu51 (Glu 2 of SEQ ID NO:4) is also mobile and invisible in electron density maps as is the C-terminal residue Ala46 (Ala128 of SEQ ID NO:4). The observed terminal residues are Ser52 and Ser45 (Ser3 and Ser127 of SEQ ID NO:4), which show distinctly higher B-values for main- and side-chain atoms than found in the rest of the structure. A comparison of CP51/46 in this region with unbound and biotin bound wild-type structures reveals more similarity to the unbound structure, where the binding loop adopts a more mobile open conformation than in the complex. The last β-sheet hydrogen bond in the wild-type unbound state is between atoms Ser45 N (Ser127 of SEQ ID NO:4) and Ser52 O (Ser3 of SEQ ID NO:4). This interaction is also observed in CP51/46 where the distances in the four subunits range from 3.0 to 3.4 Å.

The termini in the four subunits in the biotin complex of CP51/46 align well with those residues in the wild-type structure. In subunits 1, 2 and 3, residue 46 (Ala128 of SEQ ID NO:4) was observed in the electron density maps. In subunit 4, an additional residue 51 (Glu2 of SEQ ID NO:4) was refined at the N-terminus, but the N-terminal methionine was never observed. There is a slight separation of the termini from each other than results in breakage of the hydrogen bond between the Ser45 (Ser127 of SEQ ID NO:4) nitrogen and the Ser52 (Ser3 of SEQ ID NO:4) oxygen. This was also observed in the structures of the wild-type streptavidin (Freitag S, et al. (1997) Protein Sci 6:1157–1166). Breakage of that hydrogen bond is accompanied by the formation of a hydrogen bond between Ser45 Oγ and the ureido nitrogen atom of the bound biotin.

In all four subunits in the CP51/46-biotin complex, electron density for biotin was detected in the same orientation as in the wild-type biotin complex (FIG. 3). The only difference in the hydrogen bonding patterns for biotin between wild-type and CP51/46 involve the carboxyl O1 atom. In this wild-type complex, this oxygen atom is hydrogen bonded to the amide of Asn49 (SEQ ID NO:1), but the deletion of the binding loop removes this interaction. Crystal packing interactions replace the loop interactions in subunit 2 (as described above). All other first shell hydrogen bonds are very similar to those found in the wild-type complex (Freitag S, et al. (1997) Protein Sci 6:1157–1166). The second shell of hydrogen bonds is disturbed by deletion of residue Val47 which interacts with Ser45 (Ser127 of SEQ ID NO:4) in the wild-type protein.

It might be anticipated that deletion of the loop that closes over the biotin site would result in significantly larger solvent accessible surfaces for the biotin ligands in CP51/46. In fact, the changes are not all that large. The average solvent accessible surface for biotin in the wild-type complex is 18.3

Å$^2$, indicative of the nearly complete burial of biotin when bound to streptavidin. (The solvent accessible surface for "free" biotin is 407.2 Å$^2$). The only exposed biotin atoms are the carboxyl oxygen atoms. The accessible surface increases to 56.5 Å$^2$ for the CP51/46 complex. The oxygen atoms become more exposed as do portions of the aliphatic chain.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A circularly permuted biotin binding protein comprising a streptavidin polypeptide wherein the wild type streptavidin carboxyl terminal amino acid and the amino terminal amino acid of the wild type streptavidin have been joined directly or via a linker, and wherein new carboxyl and amino termini have been created by cleavage of the streptavidin polypeptide and the resulting circularly permuted protein binds biotin.

2. The circularly permuted biotin binding protein of claim 1, wherein the streptavidin carboxyl terminal amino acid and amino terminal amino acid are joined by a linker comprising one or more amino acids.

3. The circularly permuted biotin binding protein of claim 2, wherein the linker is a tetrapeptide comprising three glycines and one serine and wherein one glycine is connected to the carboxyl terminal amino acid and the serine is connected to the amino terminal amino acid.

4. The circularly permuted biotin binding protein of claim 1, wherein a portion of the streptavidin polypeptide is removed to form the new carboxyl and amino termini, and wherein the removed portion is non-critical for biotin binding.

5. The circularly permuted biotin binding protein of claim 4, wherein the portion of the streptavidin polypeptide that is removed is all or a portion of a flexible loop that participates in biotin binding.

6. The circularly permuted biotin binding protein of claim 5, wherein the portion of the streptavidin polypeptide that is removed is amino acid residues 47 through 50.

7. The circularly permuted biotin binding protein of claim 1, wherein the biotin binding affinity of the circularly permuted biotin binding protein is at least 25% of wild type streptavidin binding affinity.

8. The circularly permuted biotin binding protein of claim 1, wherein the biotin binding affinity of the circularly permuted biotin binding protein is between $10^7$ $M^{-1}$ and the biotin binding affinity of wild type streptavidin.

9. A method of making a circularly permuted biotin binding protein, comprising;

creating a circularly permuted biotin binding protein as defined in claim 1 by chemical synthesis, modification of an existing protein, or expression of the protein using recombinant DNA methodology.

10. The method of claim 9, comprising the steps:

reacting the streptavidin polypeptide in the presence of a linker to form covalent bonds between the linker and the carboxyl and amino termini of the streptavidin polypeptide, thus forming a circular protein; and forming new termini by opening the peptide bond joining amino acids at another location.

11. The method of claim 9, comprising the steps:

creating a polynucleotide sequence that encodes the circularly permuted biotin binding protein;

placing the polynucleotide in an expression cassette under the control of a suitable expression promoter;

expressing the protein in a host; and isolating the expressed protein.

12. The circularly permuted biotin binding protein of claim 1 wherein the streptavidin polypeptide is wild type streptavidin.

* * * * *

SEQUENCE LISTING

<160> NUMBER OF SEQ ID NOS: 4

<210> SEQ ID NO 1
<211> LENGTH: 183
<212> TYPE: PRT
<213> ORGANISM: Streptavidin
<220> FEATURE:
<221> NAME/KEY: PEPTIDE
<222> LOCATION: (1)..(183)

<400> SEQUENCE: 1

Met Arg Lys Ile Val Val Ala Ala Ile Ala Val Ser Leu Thr Thr Val
 1               5                  10                  15

Ser Ile Thr Ala Ser Ala Ser Ala Asp Pro Ser Lys Asp Ser Lys Ala
            20                  25                  30

Gln Val Ser Ala Ala Glu Ala Gly Ile Thr Gly Thr Trp Tyr Asn Gln
        35                  40                  45

Leu Gly Ser Thr Phe Ile Val Thr Ala Gly Ala Asp Gly Ala Leu Thr
    50                  55                  60

Gly Thr Tyr Glu Ser Ala Val Gly Asn Ala Glu Ser Arg Tyr Val Leu
65                  70                  75                  80

Thr Gly Arg Tyr Asp Ser Ala Pro Ala Thr Asp Gly Ser Gly Thr Ala
                85                  90                  95

Leu Gly Trp Thr Val Ala Trp Lys Asn Asn Tyr Arg Asn Ala His Ser
            100                 105                 110

Ala Thr Thr Trp Ser Gly Gln Tyr Val Gly Gly Ala Glu Ala Arg Ile
        115                 120                 125

Asn Thr Gln Trp Leu Leu Thr Ser Gly Thr Thr Glu Ala Asn Ala Trp
    130                 135                 140

Lys Ser Thr Leu Val Glu His Asp Thr Phe Thr Lys Val Lys Pro Ser
145                 150                 155                 160

Ala Ala Ser Ile Asp Ala Ala Lys Lys Ala Gly Val Asn Asn Gly Asn
                165                 170                 175

Pro Leu Asp Ala Val Gln Gln
            180

<210> SEQ ID NO 2
<211> LENGTH: 4
<212> TYPE: PRT

```
<213> ORGANISM: Artificial Sequence
<220> FEATURE:
<223> OTHER INFORMATION: Description of Artificial Sequence: peptide
      linker
<220> FEATURE:
<221> NAME/KEY: PEPTIDE
<222> LOCATION: (1)..(4)

<400> SEQUENCE: 2

Gly Gly Gly Ser
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: peptide
      linker
<220> FEATURE:
<221> NAME/KEY: PEPTIDE
<222> LOCATION: (1)..(4)

<400> SEQUENCE: 3

Val Gly Asn Ala
  1

<210> SEQ ID NO 4
<211> LENGTH: 128
<212> TYPE: PRT
<213> ORGANISM: Artificial Sequence
<220> FEATURE:
<223> OTHER INFORMATION: Description of Artificial Sequence: Circularly
      Permuted Streptavidin- CP51/46
<220> FEATURE:
<221> NAME/KEY: PEPTIDE
<222> LOCATION: (1)..(128)

<400> SEQUENCE: 4

Met Glu Ser Arg Tyr Val Leu Thr Gly Arg Tyr Asp Ser Ala Pro Ala
  1               5                  10                  15

Thr Asp Gly Ser Gly Thr Ala Leu Gly Trp Thr Val Ala Trp Lys Asn
                 20                  25                  30

Asn Tyr Arg Asn Ala His Ser Ala Thr Thr Trp Ser Gly Gln Tyr Val
             35                  40                  45

Gly Gly Ala Glu Ala Arg Ile Asn Thr Gln Trp Leu Leu Thr Ser Gly
         50                  55                  60

Thr Thr Glu Ala Asn Ala Trp Lys Ser Thr Leu Val Glu His Asp Thr
 65                  70                  75                  80

Phe Thr Lys Val Lys Pro Ser Ala Ala Ser Gly Gly Gly Ser Ala Glu
                 85                  90                  95

Ala Gly Ile Thr Gly Thr Trp Tyr Asn Gln Leu Gly Ser Thr Phe Ile
            100                 105                 110

Val Thr Ala Gly Ala Asp Gly Ala Leu Thr Gly Thr Tyr Glu Ser Ala
            115                 120                 125
```